(12) United States Patent
Craven

(10) Patent No.: US 8,052,738 B2
(45) Date of Patent: Nov. 8, 2011

(54) INTRALUMINAL FLEXIBLE STENT DEVICE

(75) Inventor: Michael Craven, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 489 days.

(21) Appl. No.: 12/052,269

(22) Filed: Mar. 20, 2008

(65) Prior Publication Data

US 2009/0240319 A1 Sep. 24, 2009

(51) Int. Cl.
*A61F 2/06* (2006.01)
(52) U.S. Cl. ...................................... 623/1.16
(58) Field of Classification Search ........ 623/1.15–1.22, 623/1.3, 1.31
See application file for complete search history.

(56) References Cited

U.S. PATENT DOCUMENTS

| | | | |
|---|---|---|---|
| 5,716,396 A | 2/1998 | Williams, Jr. | |
| 6,878,162 B2 * | 4/2005 | Bales et al. | 623/1.15 |
| 2002/0111669 A1 | 8/2002 | Pazienza et al. | |
| 2004/0073290 A1 | 4/2004 | Chouinard | |
| 2005/0096727 A1 | 5/2005 | Allen et al. | |
| 2005/0107865 A1 * | 5/2005 | Clifford et al. | 623/1.16 |
| 2007/0179593 A1 * | 8/2007 | Fierens et al. | 623/1.39 |

* cited by examiner

*Primary Examiner* — S. Thomas Hughes
*Assistant Examiner* — Katherine M Shi

(57) ABSTRACT

A stent made up of at least two connected bands, each band having a pattern of undulations formed from long, short and mid-sized segments connected together by turns. In particular, the pattern includes a repeating series having five segments: a long segment, a short segment, a mid-sized segment, a mid-sized segment, a short segment (LSMMS). When adjacent bands are connected together to form the stent body, the LSMMS segment configuration forms a series of consecutive tapered gaps between the consecutive unconnected close ended turns of adjacent bands which provide greater flexibility for the stent. The series of consecutive tapered gaps allow the stent to flex with little or no interference with adjacent bands when the stent is tracked around a small radius bend in a vessel. In addition, the length of the longest rigid element of the stent is decreased to further improve flexibility. A rigid element is formed by the lengths of the segments on both sides of a connection between adjacent bands. By decreasing the length of this rigid element, the length which must be tracked around the bends of a vessel is shortened and thus the stent is easier to advance.

14 Claims, 10 Drawing Sheets

INTRALUMINAL FLEXIBLE STENT DEVICE

FIELD OF THE INVENTION

The present invention is directed to intraluminal stents for use in maintaining open collapsed lumen walls, the intraluminal stent having extreme flexibility for being tracked around bends of a vessel having small radii.

BACKGROUND OF THE INVENTION

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries, such as those located within the coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

For example, stent prostheses have been previously disclosed for implantation within body lumens. Various stent designs have been previously disclosed for providing artificial radial support to the wall tissue, which forms the various lumens within the body, and often more specifically within the blood vessels of the body.

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty," "PTA" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. In some instances the vessel restenoses chronically, or closes down acutely, negating the positive effects of the angioplasty procedure.

To provide radial support to the treated vessel in order to prolong the positive effects of PTCA, a stent may be implanted in conjunction with the procedure. Effectively, the stent overcomes the natural tendency of the vessel walls of some patients to close back down, thereby maintaining a more normal flow of blood through that vessel than would be possible if the stent were not in place. Under this procedure, the stent may be collapsed to an insertion diameter and inserted into a body lumen at a site remote from the diseased vessel. The stent may then be delivered to the desired site of treatment within the affected lumen and deployed to its desired diameter for treatment.

Access to a treatment site is most often reached from the femoral artery. A flexible guiding catheter is inserted through a sheath into the femoral artery. The guiding catheter is advanced through the femoral artery into the iliac artery and into the ascending aorta. Further advancement of the flexible catheter involves the negotiation of an approximately 180 degree turn through the aortic arch to allow the guiding catheter to descend into the aortic cusp where entry may be gained to either the left or the right coronary artery, as desired.

Because the procedure requires insertion of the stent at a site remote from the site of treatment, the device must be guided through the potentially tortuous conduit of the body lumen to the treatment site. Therefore, the stent must be capable of being reduced to a small insertion diameter and must be flexible.

One stent configuration includes a plurality of wavelike bands having straight segments and turns (i.e., alternating turns facing opposite longitudinal directions). The bands are connected together to form an expandable tubular prosthesis. As the stent is tracked around bends of a vessel having small radii, the turns of adjacent bands may be forced together on the side of the stent adjacent to the inner side of the vessel bend. Often, the turns of adjacent bands on the inside of the vessel bend will interfere with each other or overlap. Such overlapping creates greater strains and an increased potential for permanent deformation of the stent segments in that immediate area.

Thus, it is desirable to have a flexible stent device which is designed so that interference between adjacent bands of the stent does not occur when the stent is tracked to the target location.

BRIEF SUMMARY OF THE INVENTION

The present invention is directed to an intraluminal stent device that solves many of the problems that occur when a stent is tracked through a potentially winding body conduit such as a blood vessel. In particular, stent bands of the present invention use a combination of short, mid-sized, and long segments to form a series of consecutive tapered gaps between unconnected closed-ended turns of adjacent bands when adjacent bands are connected together to form the stent body. The series of consecutive tapered gaps provide greater flexibility for the stent when the stent is tracked around a small radius bend in a vessel.

In one embodiment, the stent has generally undulating bands connected together. Each band has a pattern of undulations formed from long, short and mid-sized segments connected together by turns. The segments and turns form peaks and valleys of the stent, by which adjacent bands may be connected. In one particular embodiment, the pattern includes a repeating series of five segments and five turns which connect the segments together. The repeating series includes a long segment and a first short segment coupled by a first turn. The first short segment is coupled to a first mid-sized segment by a second turn. The first mid-sized segment is coupled to a second mid-sized segment by a third turn. The second mid-sized segment is coupled to a second short segment by a fourth turn, and the second short segment is coupled to the next series by a fifth turn. The order of the five segments has a LSMMS configuration (long, short, mid-sized, mid-sized, short). When adjacent bands are connected together to form the stent body, the LSMMS series having various segment lengths form a series of consecutive tapered gaps which provide greater flexibility for the stent. For example, the series of consecutive tapered gaps between the unconnected closed-ended turns of adjacent bands allow the stent to flex with little or no interference with adjacent bands when the stent is tracked around a small radius bend in a vessel.

The consecutive tapered nature of the series of gaps is advantageous in that the larger gaps optimally occur between turns of adjacent bands which generally experience the greatest amount of interference when the stent is tracked around a small radius bend in a vessel. Further, the smaller gaps also add to the stent body's flexibility while simultaneously providing greater scaffolding than that provided by the larger gaps. Greater scaffolding means that more area of the vessel walls is being supported directly by parts of the stent.

Another important aspect of the present invention includes minimizing the length of the longest rigid element of the stent to further improve flexibility. The longest rigid element of a stent body occurs at the location of a connection between adjacent bands. The lengths of the segments on both sides of the connection essentially form a rigid element which must be tracked around the bends of a vessel. By minimizing the length of this rigid element, the length which must be tracked around the bends of a vessel is shortened and thus the stent is easier to advance.

Adjacent bands may be formed from a toroid bent into the particular pattern. Thus, each band may be connected to an adjacent band by welding (or utilizing any appropriate type of mechanical connection) the turns to each other. Alternatively, the bands may be formed connected as a unitary structure.

The bands may be placed onto a balloon of a balloon catheter for expansion within a body lumen or they may naturally occur in an expanded condition and may be collapsed, reducing the overall profile for delivery. Once at the treatment site, the stent may be expanded to its natural condition.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Figure 1:
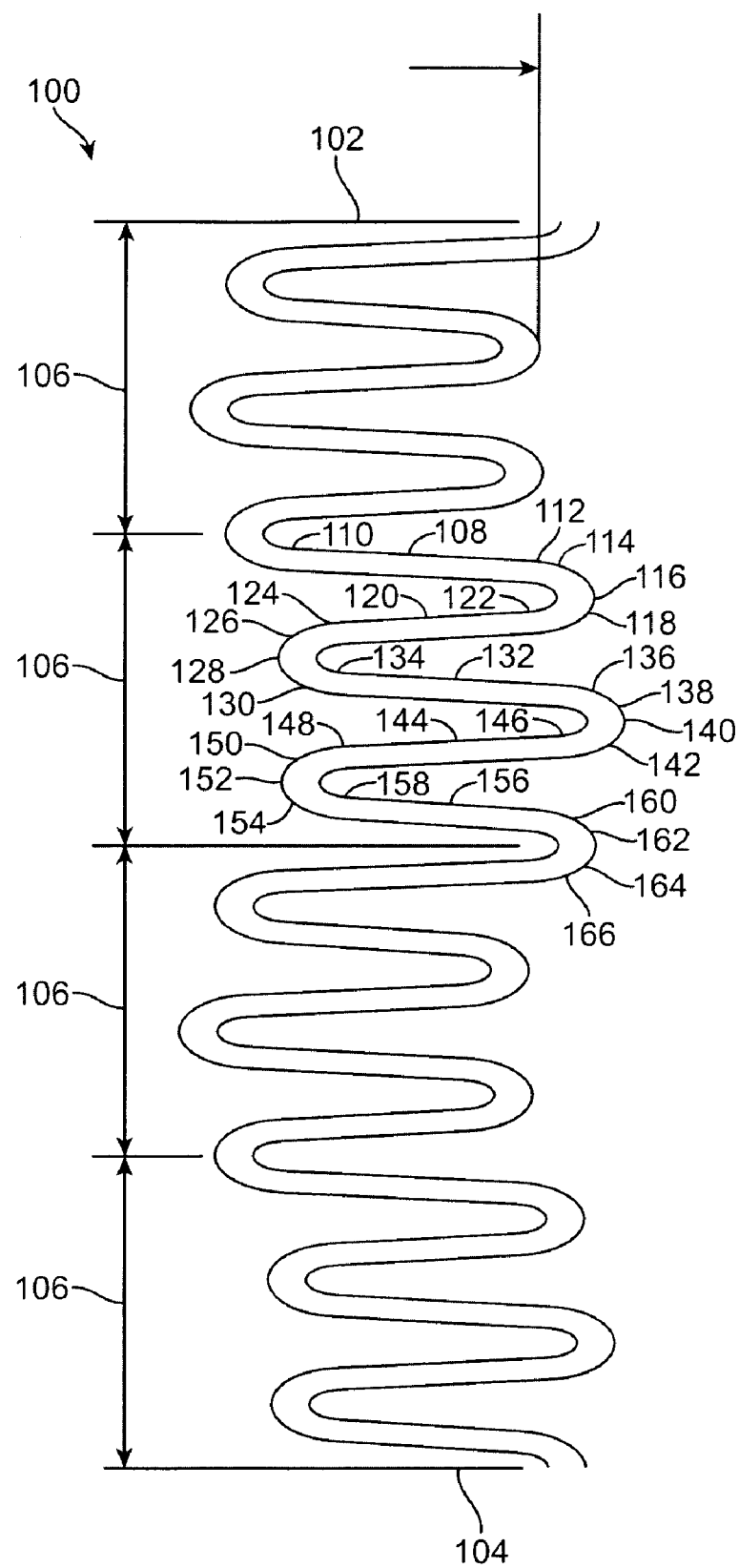
FIG. 1 is a plan view of a flattened band of the present invention.

Specific embodiments of the present invention are now described with reference to the figures, wherein like reference numbers indicate identical or functionally similar elements. The drawing in which an element first appears is typically indicated by the leftmost digit(s) in the corresponding reference number. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

The present invention generally is directed to a stent made from generally circular single bands having a uniquely defined undulating shape. Bands are aligned on a common longitudinal axis to form a generally cylindrical body having a radial and longitudinal axis. FIG. 1 shows a single band 100 of the present invention. Band 100 is shown in a schematic, as if the generally circular band 100 has been cut between ends 102 and 104 and the band 100 has been laid out flat, as if made from a ribbon bent into a sinusoidal shape. One skilled in the art can appreciate that a band 100 of the present invention may be manufactured in a variety of ways, which are discussed in further detail below. Thus, band 100 may be made flat, as shown in FIG. 1, rounded, elliptical, or have a variety of other cross-sections depending upon the desired features of the stent. Thus, a stent of the present invention is not limited to the ribbon structure shown in FIG. 1.

The generally cylindrical bands and stents are shown in FIGS. 2-8 and 10 in a flattened state, such as the band 100 shown in FIG. 1. However, one skilled in the art can appreciate that the stents and bands 100 depicted therein are intended to be used in a cylindrical body.

When viewed flat, each band 100 is a wire having an undulating pattern. The pattern includes a repeating series 106 of segments and turns. In a first embodiment depicted in FIGS. 1-4, band 100 is formed from a closed toroid wire which is bent into the structure shown in FIG. 1. Thus, segments and turns are not necessarily coupled together at the ends, but are naturally continuing one into another. Other embodiments may be manufactured differently, such that some portions may be mechanically coupled together via welding, soldering, adhesive or another bonding or another mechanical connection method. However, to describe the particular structure of band 100, various segments and turns may be described as being connected or coupled to each other. Thus, the terms "connect with," "connected," or "coupled" may mean either naturally continuing (or flowing together) or mechanically coupled together.

The repeating series 106 has five total segments, including a long segment 108, a first short segment 120, a first mid-sized segment 132, a second mid-sized segment 144, and a second short segment 156. First and second short segments 120, 156 are preferably the same length, while first and second mid-sized segments 132, 144 are preferably the same length. Short segments 120, 156 are shorter than mid-sized segments 132, 144 and mid-sized segments 132, 144 are shorter than long segment 108. The order of the five segments of series 106 has a LSMMS configuration (long, short, mid-sized, mid-sized, short).

In addition, the series 106 has five total turns, including a first turn 116, a second turn 128, a third turn 140, a fourth turn 152, and a fifth turn 164. The segments and turns form valleys and peaks of the stent, in which peaks face the opposite longitudinal direction than valleys. For the purpose of this description, peaks and valleys may face either longitudinal direction provided that all peaks face one longitudinal direction and all valleys face the opposite longitudinal direction. Thus, when two bands are side by side, flipping one band in the opposite direction would by definition convert all the peaks to valleys and valleys to peaks. For ease of description in this application, peaks are formed by turns to the right side of segments such that the closed end of the turn of a peak faces to the right and the open end of a peak faces to the left. Similarly, valleys are formed by turns to the left of segments such that the closed end of a turn of a valley faces left and the open end of a turn of a valley faces right. Thus, turns 116, 140, and 164 shown in FIG. 1 are peaks and turns 128 and 152 shown in FIG. 1 are valleys. The five turns 116, 128, 140, 152, and 164 connect the segments 108, 120, 132, 144, and 156 of the series 106 together, as described below.

Long segment 108 connects with the previous series 106 at a first end 110. A second end 112 of long segment 108 connects with a first end 114 of a first turn 116.

A second end 118 of first turn 116 connects with a first end 122 of a first short segment 120. First short segment 120 is shorter than long segment 108. A second end 124 of first short segment 120 connects with a first end 126 of a second turn 128. Second turn 128 faces the opposite longitudinal direction as first turn 116.

A second end 130 of second turn 128 connects with a first end 134 of a first mid-sized segment 132. First mid-sized segment 132 is longer than first short segment 120, but shorter than long segment 108. A second end 136 of first mid-sized segment 132 connects with a first end 138 of a third turn 140. Third turn 140 faces the opposite longitudinal direction as second turn 128, thus facing the same longitudinal direction as first turn 116.

A second end 142 of third turn 140 connects with a first end 146 of a second mid-sized segment 144. Second mid-sized segment 144 is preferably the same length as first mid-sized segment 132, but may be a different length. Second mid-sized segment 144 is longer than first short segment 120, but shorter than long segment 108. A second end 148 of mid-sized segment 144 connects with a first end 150 of a fourth turn 152. Fourth turn 152 faces the opposite longitudinal direction as third turn 140, thus facing the same longitudinal direction as second turn 128.

A second end 154 of fourth turn 152 connects with a first end 158 of a second short segment 156. Second short segment 156 is preferably the same length as first short segment 120, but may be a different length. Second short segment 156 is shorter than long segment 108, and is also shorter than both first and second mid-sized segments 132, 144. A second end 160 of short segment 156 connects with a first end 162 of a fifth turn 164. Fifth turn 140 faces the opposite longitudinal direction as fourth turn 528, thus facing the same longitudinal direction as both first turn 116 and third turn 140. The second end 166 of the fifth turn 164 connects with the next adjacent series 106.

Thus, band 100 has regions of shorter segments, regions of mid-sized segments, and regions of longer segments within the same circular band 100. A stent having all of these regions can be more easily tracked in body vessels having bends of small radii, as will be described in detail more fully below.

Since third turn 140 is connected to first mid-sized segment 132 and second mid-sized segment 144 on its two ends 138 and 142, third turn 140 forms a peak that is longitudinally offset from peaks formed at first and fifth turns 116, 164 of the series 106. In the particular series 106 labeled in FIG. 1, third turn 140 is disposed farther to the right than first turn 116 or fifth turn 164.

Fourth turn 152 may be longitudinally aligned with second turn 128, or longitudinally offset. Preferably, second turn 128 is longitudinally aligned with fourth turn 152, because in a preferred embodiment, short segments 120, 156 are the same length and mid-sized segments 132, 144 are the same length. However, in other embodiments, short segments 120, 156 may be of different lengths and mid-sized segments 132, 144 may be of different lengths.

In the first embodiment depicted in FIGS. 1-4, each series 106 is connected to an identical adjacent series 106. However, one skilled in the art can appreciate that each series 106 may have different sized long segments 108, first and second short segments 120 and 156, and first and second mid-sized segments 132 and 144 from the series 106 that is before or after it. In addition, series 106 may be connected to a different adjacent series (i.e., a series which does not have the LSMMS configuration of series 106), as will be described in additional embodiments below.

FIG. 1 shows band 100 having four full series 106. However, any number of series 106 may be used in band 100. For example, when band 100 is to be used in body lumens having large diameters, more series 106 may be used. Meanwhile, as few as two series 106 may be used in a band 100 for use in body lumens with small diameters.

In general, long segment 108, first mid-sized segment 132, and second short segment 156 are parallel, and first short segment 120 and second mid-sized segment 144 are parallel. In FIG. 1, long segment 108, first mid-sized segment 132, and second short segment 156 generally lean to the right, while first short segment 120 and second mid-sized segment 144 lean generally to the left. However, long segment 108, first mid-sized segment 132, and second short segment 156 may lean generally to the left, while first short segment 120 and second mid-sized segment 144 lean generally to the right, such as series 106 of band 100*b* as shown and described in FIG. 2.

Figure 2:
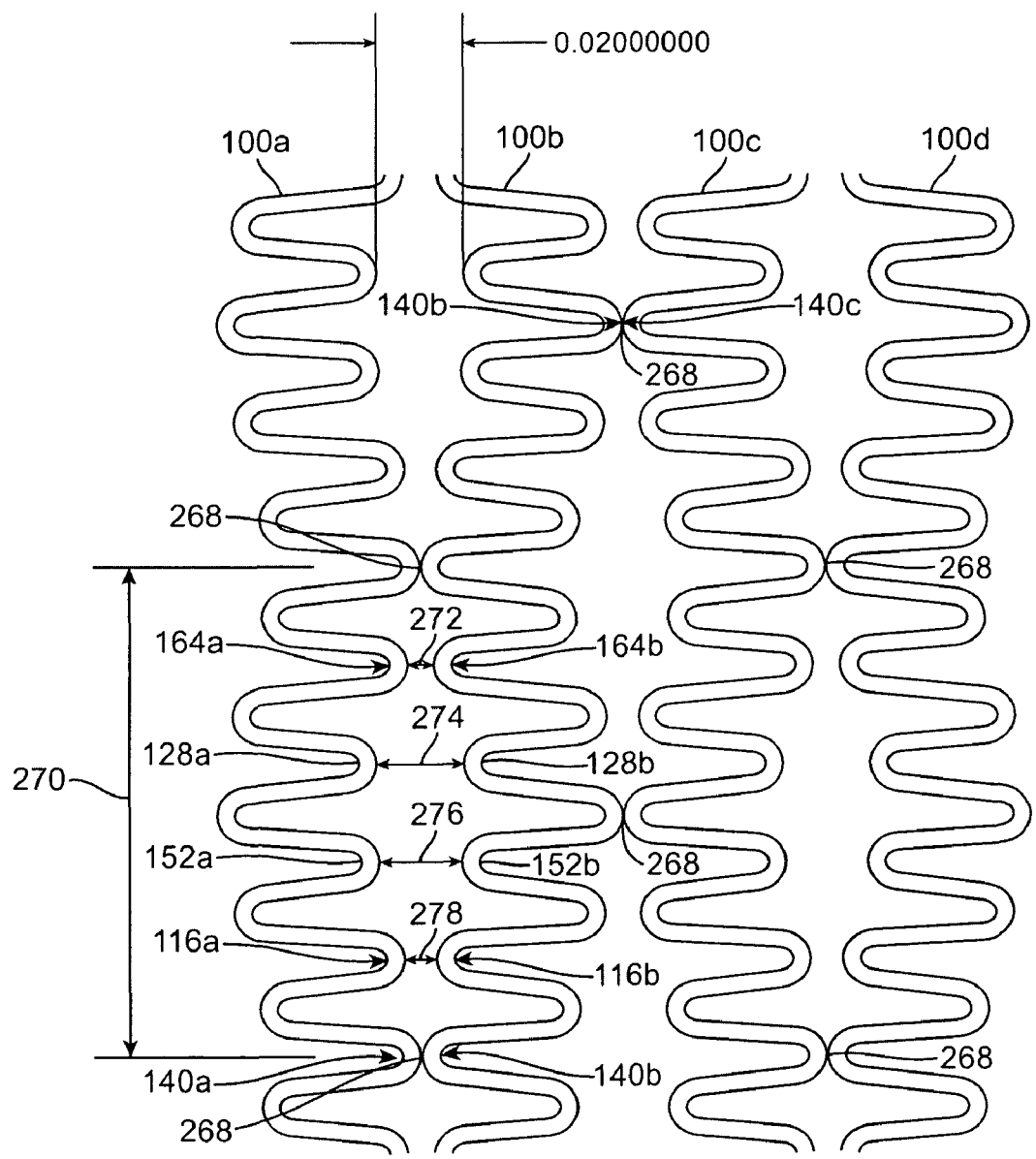
FIG. 2 is a plan view of four flattened aligned bands of the present invention with connections between adjacent bands.

FIG. 2 shows a portion of a stent having four bands 100 (100*a*, 100*b*, 100*c*, and 100*d*) connected at connections 268. Bands 100*a* and 100*b* are functionally the same. Band 100*b* is a mirror image of band 100*a*, and band 100*d* is a mirror image of band 100*c*. Therefore, bands 100*a*, 100*b*, 100*c*, and 100*d* each include a substantially similar pattern of segments and turns forming peaks and valleys. The bands are aligned to form adjacent bands such that each peak of a band is aligned with a valley of an adjacent band and each valley of a band is aligned with a valley of an adjacent band. For example, the peak at first turn 116*a* of band 100*a* is aligned with the valley formed by first turn 116*b* of band 100*b*. Similarly, the peaks at third and fifth turns 140*a*, 164*a* of band 100*a* are aligned with the valleys formed at third and fifth turns 140*b*, 164*b* of band 100*b*. Similarly, the valleys formed at second and fourth turns 128*a*, 152*a* of band 100*a* are aligned with the peaks formed at second and fourth turns 128b, 152b of band 100b. Where a peak of band 100a is aligned with a valley of band 100b, it can be seen that the closed end of the peak of band 100a faces the closed end of the valley of band 100b. Thus, when a valley of band 100a is aligned with a peak of band 100b, it can be seen that the open end of the valley of band 100a faces the open end of the peak of band 100b.

At least one connection 268 is formed where closed ends of turns of adjacent bands are aligned. In the embodiment of FIG. 2, the offset peaks and valleys formed by first and second mid-sized segments 132, 144 of a band are connected to the offset peaks and valleys formed by first and second mid-sized segments 132, 144 of an adjacent band. The offset peaks and valleys of each band 100a, 100b, 100c, and 100d are formed by third turn 140 of the series 106 as described above, having first and second mid-sized segments 132, 144 on either side of third turn 140. For example, connection 268 is illustrated on FIG. 3 between a peak at third turn 140a of band 100a and a valley at third turn 140b of the adjacent band 100b.

Connections 268 are preferably formed by welding the turns together, such as by resistance welding, friction welding, laser welding or another form of welding such that no additional materials are used to connect bands 100. Alternatively, bands 100 can be connected by soldering, by the addition of a connecting element between the turns, or by another mechanical method. Further, as discussed above, the stent may be formed pre-connected as a unitary structure, such as by laser cutting or etching the entire stent body from a hollow tube or sheet. Other connections or ways to connect bands would be apparent to one skilled in the art and are included herein.

When adjacent bands 100 are connected together, a series 270 of consecutive tapered gaps is formed between consecutive unconnected aligned closed ends of turns of adjacent bands due to the various segment lengths of the LSMMS series described above. The series 270 of consecutive tapered gaps allows the stent to flex with little or no interference between adjacent bands when the stent is tracked around a small radius bend in a vessel.

The series 270 of consecutive tapered gaps includes four gaps 272, 274, 276, 278 between connections 268. If first and second short segments 120, 156 are the same length and first and second mid-sized segments 132, 144 are the same length, gaps 274 and 276 will be of equal length and gaps 272 and 278 will be of equal length. Due to the length of long segment 108, gaps 274 and 276 are generally larger than gaps 272 and 278. The larger gaps 274 and 276 occur at the second and fourth turns of each band, while smaller gaps 272 and 278 occur at the fifth and first turns of each band, respectively. The larger gaps 274, 276 optimally occur between aligned closed ends of turns of adjacent bands which generally experience the greatest amount of interference when the stent is tracked around a small radius bend in a vessel.

Thus, the LSMMS series of various segment lengths form a series 270 of consecutive tapered gaps between the unconnected aligned closed ends of turns of adjacent bands which provides greater flexibility for the stent, and allows the stent to flex with little or no interference with adjacent bands when the stent is tracked around a small radius bend in a vessel. The consecutive tapered nature of series 270 is advantageous in that larger gaps 274, 276 optimally occur between turns of adjacent bands which generally experience the greatest amount of interference when the stent is tracked around a small radius bend in a vessel. Smaller gaps 272, 278 also add to the stent body's flexibility, while simultaneously providing greater scaffolding than that provided by larger gaps 274, 276. Greater scaffolding means that more area of the vessel walls is being supported directly by parts of the stent.

In addition to providing flexibility through the series 270 of consecutive tapered gaps, another important aspect of the present invention includes decreasing the length of the longest rigid element of the stent to further improve flexibility. The longest rigid element of a stent body occurs at the location of a connection 268. Connection 268 and the longest two segments on either side of connection 268 essentially form a rigid element which must be tracked around the bends of a vessel. By minimizing the length of this rigid element, the length which must be tracked around the bends of a vessel is shortened and thus the stent is easier to advance.

Figure 3:
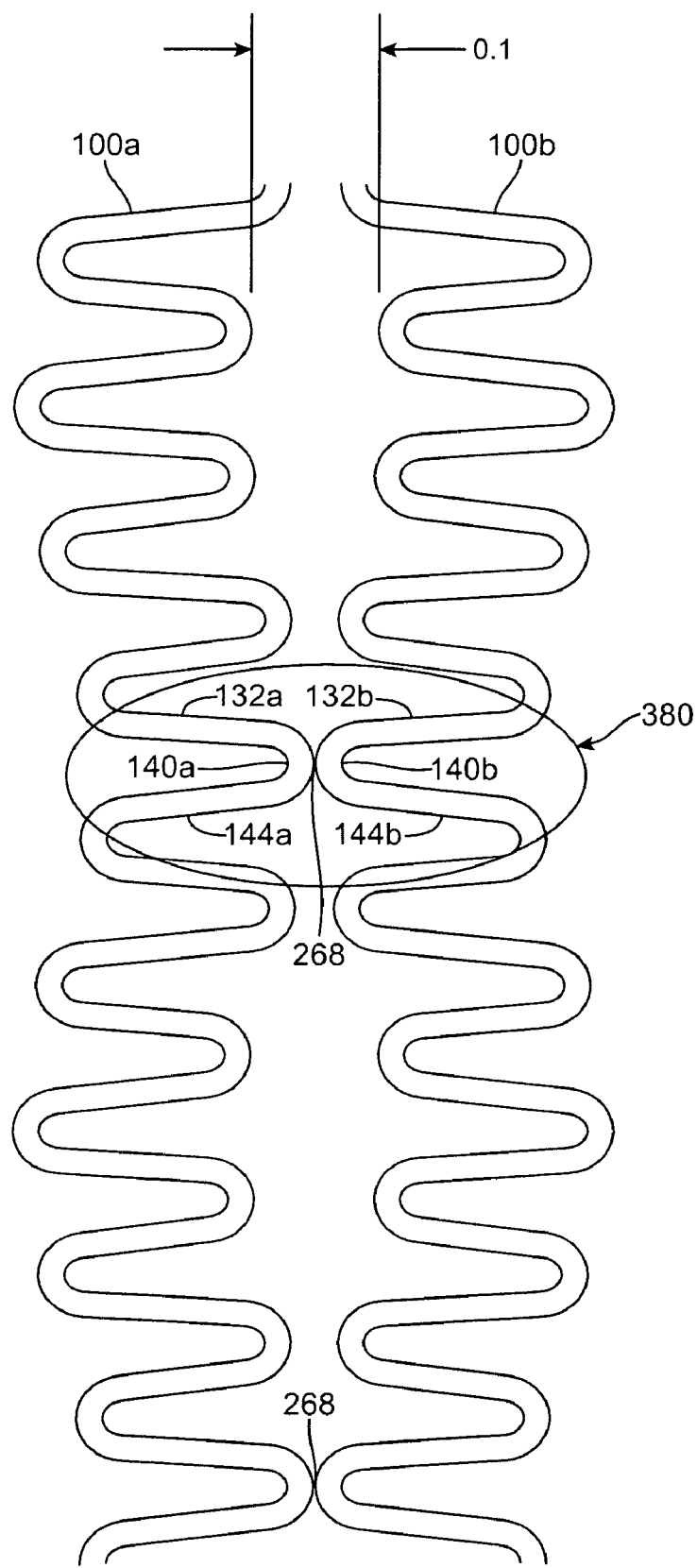
FIG. 3 is another plan view of two flattened aligned bands of the present invention with connections between adjacent bands.

FIG. 3 illustrates the concept of a minimized rigid element 380. FIG. 3 shows a stent having two bands 100 (100a, 100b) connected at connections 268. Bands 100a and 100b are functionally the same. Band 100b is a mirror image of band 100a. The offset peaks and valleys formed by first and second mid-sized segments 132a, 144a of a band 100a are connected to the offset peaks and valleys formed by first and second mid-sized segments 132b, 144b of an adjacent band 100b. The offset peaks and valleys of each band 100a, 100b are formed by the third turns of the repeating series 106 as described above, having first and second mid-sized segments 132, 144 on either side of the third turns. For example, connection 268 is illustrated on FIG. 3 between third turn 140a of band 100a and third turn 140b of the adjacent band 100b. The length of rigid element 380 is decreased since mid-sized segments are on both sides of connection 268.

Figure 4:
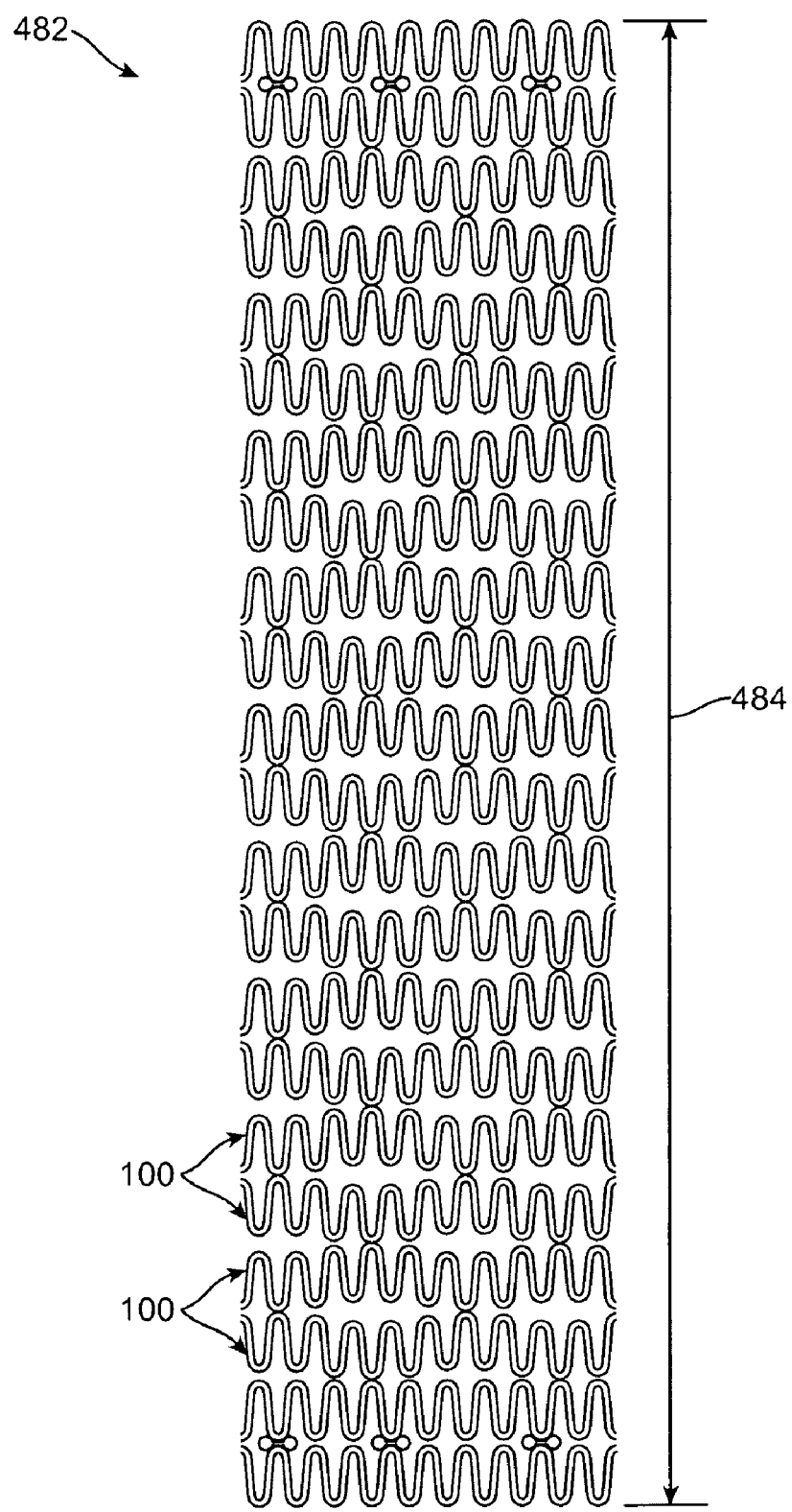
FIG. 4 is a plan view of a stent having multiple flattened aligned bands of the present invention with connections between adjacent bands.

FIG. 4 shows a stent 482 having more than two bands 100 connected together to form a length 484 of the stent body. One of ordinary skill in the art will appreciate that stent 482 can have any number of bands 100 depending upon the desired length of stent 482.

A stent can be expanded in several ways. Some stents are collapsed from a natural expanded shape into a collapsed state for delivery to the vessel. When a sleeve holding the stent in the collapsed shape is removed, the stent expands to its natural expanded state in the correct position within the lumen. Other stents are heat expandable. Once placed in the correct position, the stent is subjected to a heat source, which causes the expansion of the stent through a chemical reaction or natural thermal expansion, depending upon the material from which the stent is made. Still other stents are collapsed on top of a balloon, such as the type of balloon used in an angioplasty procedure. As the balloon expands, it physically forces the stent to expand at the same time. The balloon is then collapsed leaving the stent in the expanded position.

Figure 9:
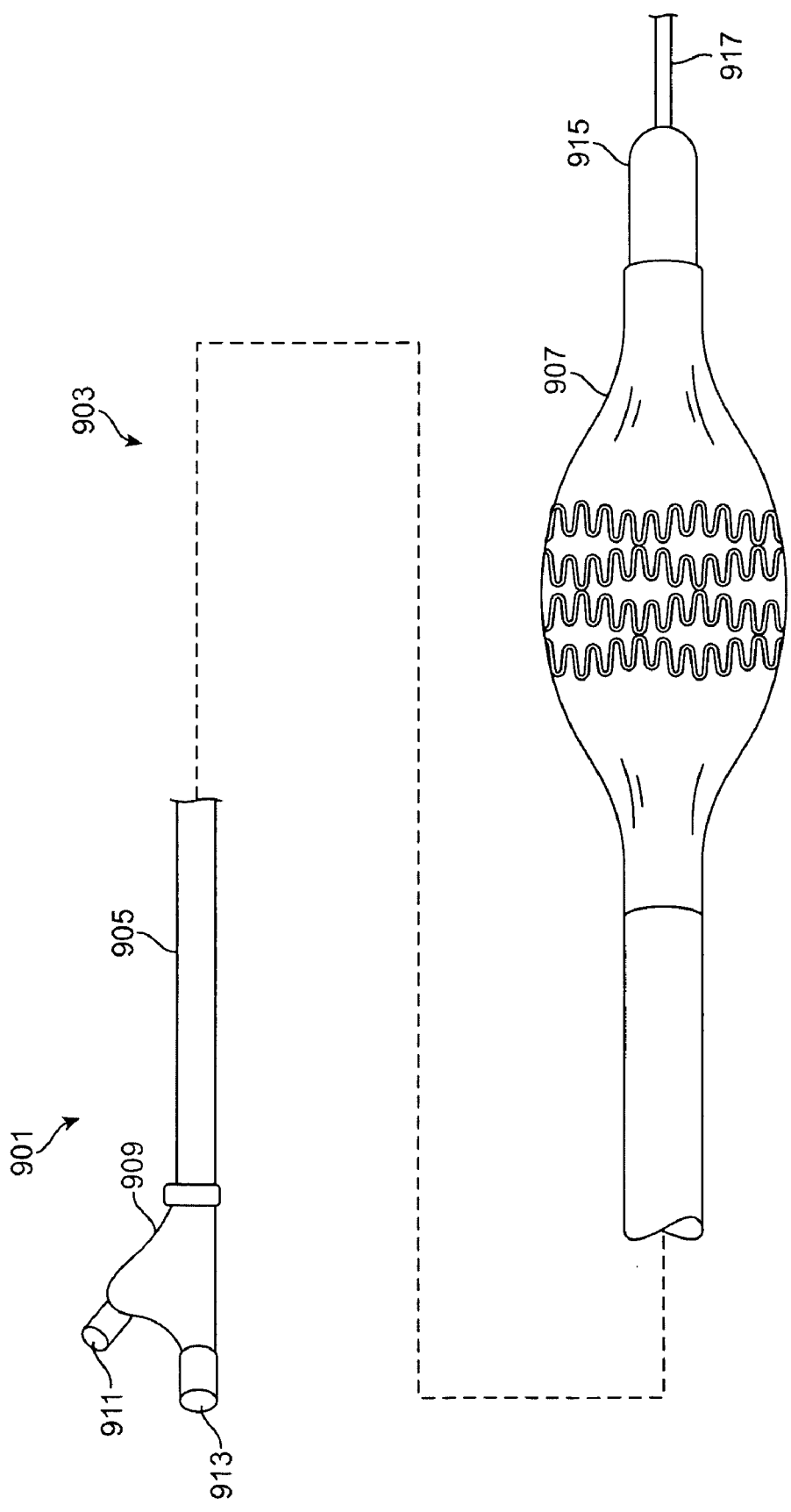
FIG. 9 is a side elevational view of a stent according to an embodiment of the present invention loaded onto a balloon of a balloon catheter.

Preferably, the stent of the present invention is formed in a natural state, crimped onto a balloon dilation catheter for delivery to a treatment site and expanded by the radial force of the balloon. For example, FIG. 9 is an illustration of a stent delivery system 901 in accordance with an embodiment of the present invention. Stent delivery system 901 includes a catheter 903 having a proximal shaft 905, a guidewire shaft 915, and a balloon 907. Proximal shaft 905 has a proximal end attached to a hub 909 and a distal end attached to a proximal end of balloon 907. Guidewire shaft 915 extends between hub 909 and a distal tip of catheter 903 through proximal shaft 905 and balloon 907. Hub 909 includes an inflation port 911 for coupling to a source of inflation fluid. Inflation port 911 fluidly communicates with balloon 907 via an inflation lumen (not shown) that extends through proximal shaft 905. In addition, hub 909 includes a guidewire port 913 that communicates with a guidewire lumen (not shown) of guidewire shaft 915 for receiving a guidewire 917 there through. As described herein, guidewire shaft 915 extends the entire length of catheter 903 in an over-the-wire configuration. However, as would be understood by one of ordinary skill in the art, guidewire shaft 915 may alternately extend only within the distal portion of catheter 903 in a rapid-exchange configuration. A stent formed from in accordance with an embodiment of the present invention is positioned over balloon 907. However, one skilled in the art can appreciate that the stent of the present invention can be adapted for any type of delivery method.

The stent is preferably constructed of implantable materials having good mechanical strength. For example, a stent of one embodiment may be machined from implantable quality stainless steel bar stock. In another embodiment, a stent of the present invention could be made of any other metal suitable for implantation, such as cobalt based alloys (605L, MP35N), titanium, tantalum, superelastic nickel-titanium alloy, other biocompatible metals or thermoplastic polymers. Finally, although not required in all cases, the outside of the stent may be selectively plated with platinum to provide improved visibility during fluoroscopy.

Stents of the present invention may be formed using any of a number of different methods. For example, the stents may be formed by winding a wire or ribbon around a mandrel to form the pattern described above and then welding or otherwise mechanically connecting two ends thereof to form bands 100. Bands 100 are subsequently connected together to form the stent body. Alternatively, stents may be manufactured by machining tubing or solid stock material into toroid bands, and then bending the bands on a mandrel to form the pattern described above. Bands 100 formed in this manner are subsequently connected together to form the longitudinal stent body. Laser or chemical etching or another method of cutting a desired shape out of a solid stock material or tubing may also be used to form stents of the present invention. In this manner, bands 100 may be formed connected together such that the stent body is a unitary structure. Further, a stent of the present invention may be manufactured in any other method that would be apparent to one skilled in the art. The cross-sectional shape of the finished stent may be circular, ellipsoidal, rectangular, hexagonal rectangular, square, or other polygon, although at present it is believed that circular or ellipsoidal may be preferable.

Figure 5:
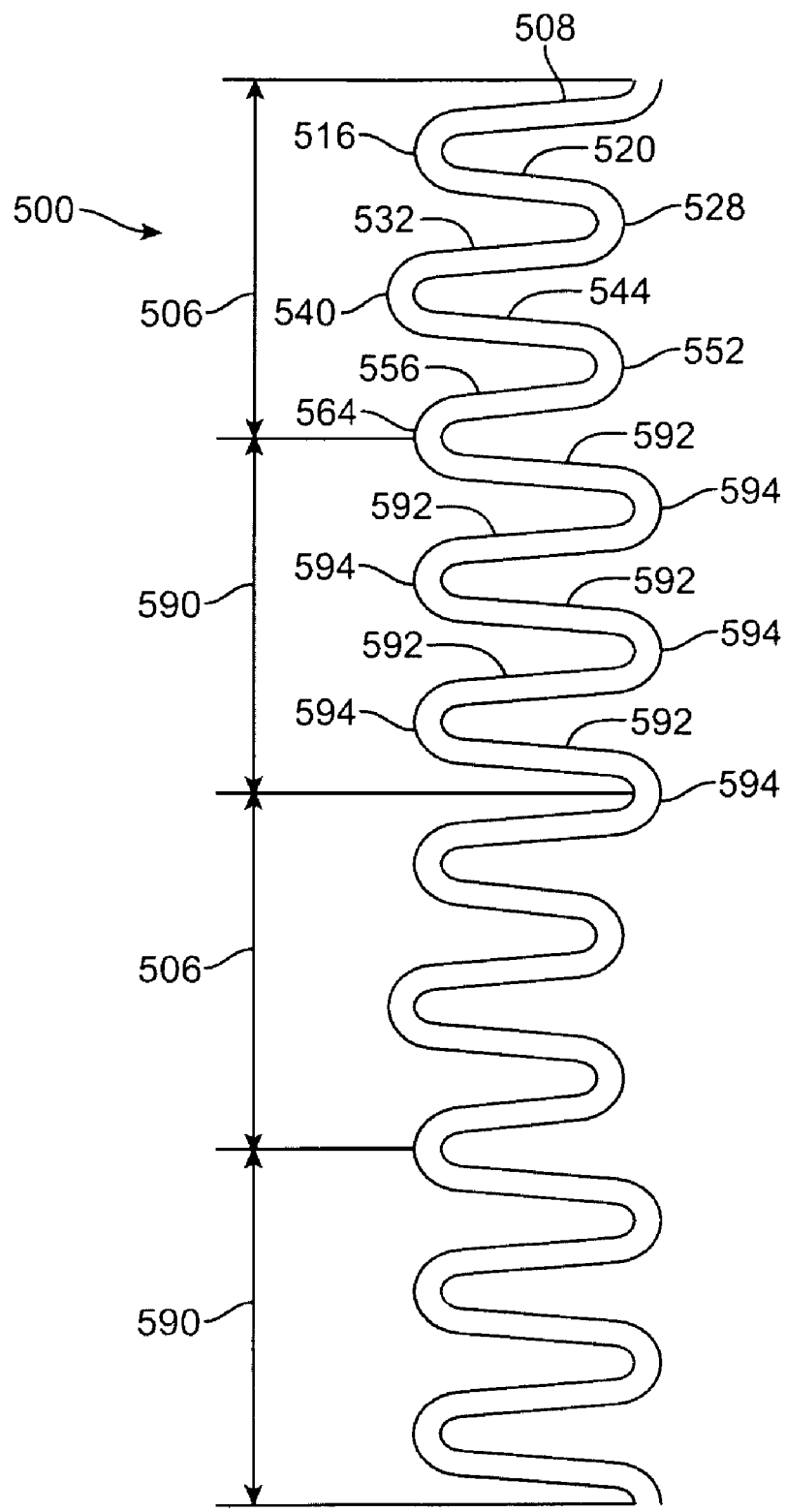
FIG. 5 is a plan view of a flattened band according to another embodiment of the present invention.

FIG. 5 shows another embodiment of the present invention, illustrated as a flattened band 500. Like band 100, band 500 is a wire having an undulating pattern. The pattern includes a repeating series 506 of segments and turns. Like series 106 of FIG. 1, the series 506 has five total segments, including a long segment 508, a first short segment 520, a first mid-sized segment 532, a second mid-sized segment 544, and a second short segment 556. First and second mid-sized segments 532, 544 are preferably the same length, while first and second short segments 520, 556 are preferably the same length. Short segments 520, 556 are shorter than mid-sized segments 532, 544, and mid-sized segments 532, 544 are shorter than long segment 508. The order of the five segments of series 506 has a LSMMS configuration (long, short, mid-sized, mid-sized, short).

In addition, the series 506 has five total turns, including a first turn 516, a second turn 528, a third turn 540, a fourth turn 552, and a fifth turn 564. The segments and turns form valleys and peaks, in which peaks face the opposite longitudinal direction than valleys. The five turns 516, 528, 540, 552, and 564 connect the segments 508, 520, 532, 544, and 556 of the series 506 together in the same fashion described above with respect to series 106. Since third turn 540 is connected to first mid-sized segment 532 and second mid-sized segment 544, third turn 540 is longitudinally offset from first turn 516 and fifth turn 564.

Figure 6:
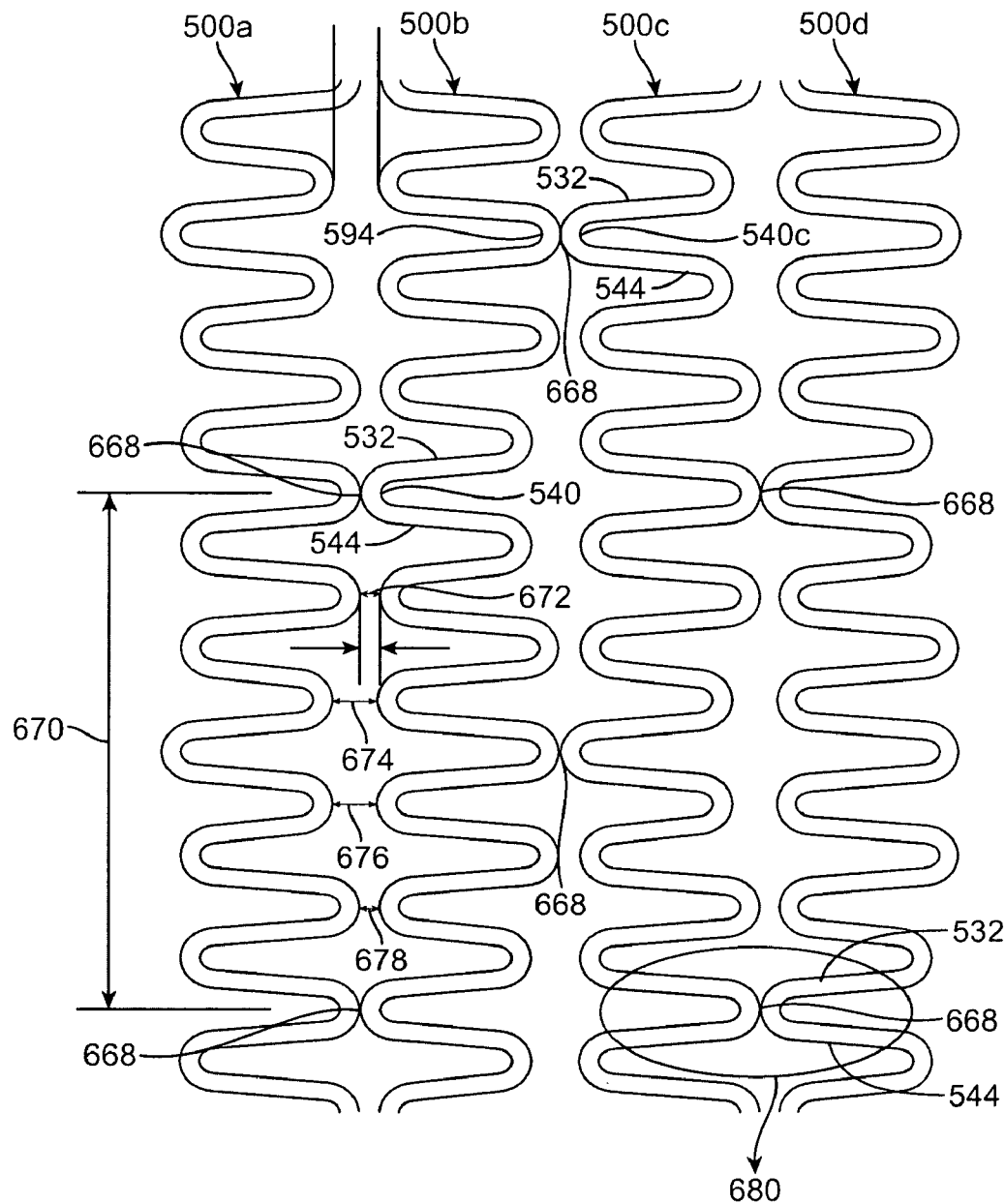
FIG. 6 is a plan view of four flattened aligned bands according to the embodiment illustrated in FIG. 5 with connections between adjacent bands.

Unlike the embodiment of FIGS. 1-4, in the embodiment depicted in FIGS. 5-6, series 506 is connected to a different adjacent series 590 (i.e., a series which does not have the LSMMS configuration of series 106 and series 506). Series 590 includes five long segments 592 connected by five turns 594. Long segments 592 are preferably substantially the same length as long segment 508 of series 506, but may be different. Band 500 of FIG. 5 illustrates a total of four series connected together in the following order: a first series 506, a first series 590, a second series 506, and a second series 590.

FIG. 6 shows a stent having four bands 500 (500a, 500b, 500c, and 500d) connected at connections 668. Bands 500a, 500b, 500c, and 500d are functionally the same. Band 500b is a mirror image of band 500a, and band 500d is a mirror image of band 500c. Therefore, bands 500a, 500b, 500c, and 500d each include a substantially similar pattern of segments and turns forming peaks and valleys. The bands are aligned to form adjacent bands such that the closed end of every other turn of a band is aligned with the closed end of every other turn of an adjacent band.

At least one connection 668 is formed aligned closed ends of turns of adjacent bands. In this embodiment of FIG. 6, connections 668 occur at each of the offset peaks and valleys of a band formed by having first and second mid-sized segments 532, 544 on either side of the peak or valley. In other words, the offset peaks and valleys formed by third turns 540 of a band are connected to the peaks and valleys formed at one of turns 594 of an adjacent band. The offset peaks and valleys of each band 500a, 500b, 500c, and 500d are formed by the third turns 540 of the repeating series 506 as described above, having first and second mid-sized segments (532, 544) on either side of the third turn 540. For example, connection 668 is illustrated on FIG. 6 between third turn 540c of series 506 on band 500c and the third turn 594 of series 590 on adjacent band 500b.

Connections 668 are preferably forming by welding the turns together, such as by resistance welding, friction welding, laser welding or another form of welding such that no additional materials are used to connect bands 500. Alternatively, bands 500 can be connected by soldering, by the addition of a connecting element between the turns, or by another mechanical method. Further, as discussed above, the stent may be formed pre-connected as a unitary structure, such as by laser cutting or etching the entire stent body from a hollow tube or sheet. Other connections or ways to connect bands would be apparent to one skilled in the art and are included herein.

When adjacent bands 500 are connected together, a series 670 of consecutive tapered gaps is formed between consecutive unconnected aligned closed ends of turns of adjacent bands. The series 670 of consecutive tapered gaps allows the stent to flex with little or no interference between adjacent bands when the stent is tracked around a small radius bend in a vessel.

The series 670 of consecutive tapered gaps includes four gaps 672, 674, 676, 678 between connections 668. If first and second mid-sized segments 532, 544 are the same length and first and second short segments 520, 556 are the same length, gaps 674 and 676 will be of equal length and gaps 672 and 678 will be of equal length. Due to the length of long segment 508, gaps 674 and 676 are generally larger than gaps 672 and 678. The consecutive tapered nature of series 670 is advantageous in that larger gaps 674, 676 optimally occur between turns of adjacent bands which generally experience interference when the stent is tracked around a small radius bend in a vessel. Smaller gaps 672, 678 also add to the stent body's flexibility, while simultaneously providing greater scaffolding than that provided by larger gaps 674, 676. Greater scaffolding means that more area of the vessel walls is being supported directly by parts of the stent.

In addition to providing flexibility through the series 670 of consecutive tapered gaps, the embodiment depicted in FIGS. 5-6 also incorporates a decreased length rigid element 680. As explained above with respect to FIG. 3, decreasing the length of the longest rigid element of the stent further improves flexibility. The longest rigid element of a stent body occurs at the location of a connection 668. Connection 668 and the longest two segments on either side of connection 668 essentially form a rigid element which must be tracked around the bends of a vessel. By decreasing the length of this rigid element, the length which must be tracked around the bends of a vessel is shortened and thus the stent is easier to advance. As described above, connections 668 occur at the offset peaks and valleys of a band formed by mid-sized segments 532, 544 of a series 506. In other words, the peaks and valleys formed by first and second mid-sized segments 532, 544 of each band 500 are connected to an aligned closed end of a turn 594 of an adjacent band. Although long segments 592 occur on one side of connection 668, the length of rigid element 680 is decreased since mid-sized segments 532 and 544 occur on the other side of connection 668.

Figure 7:
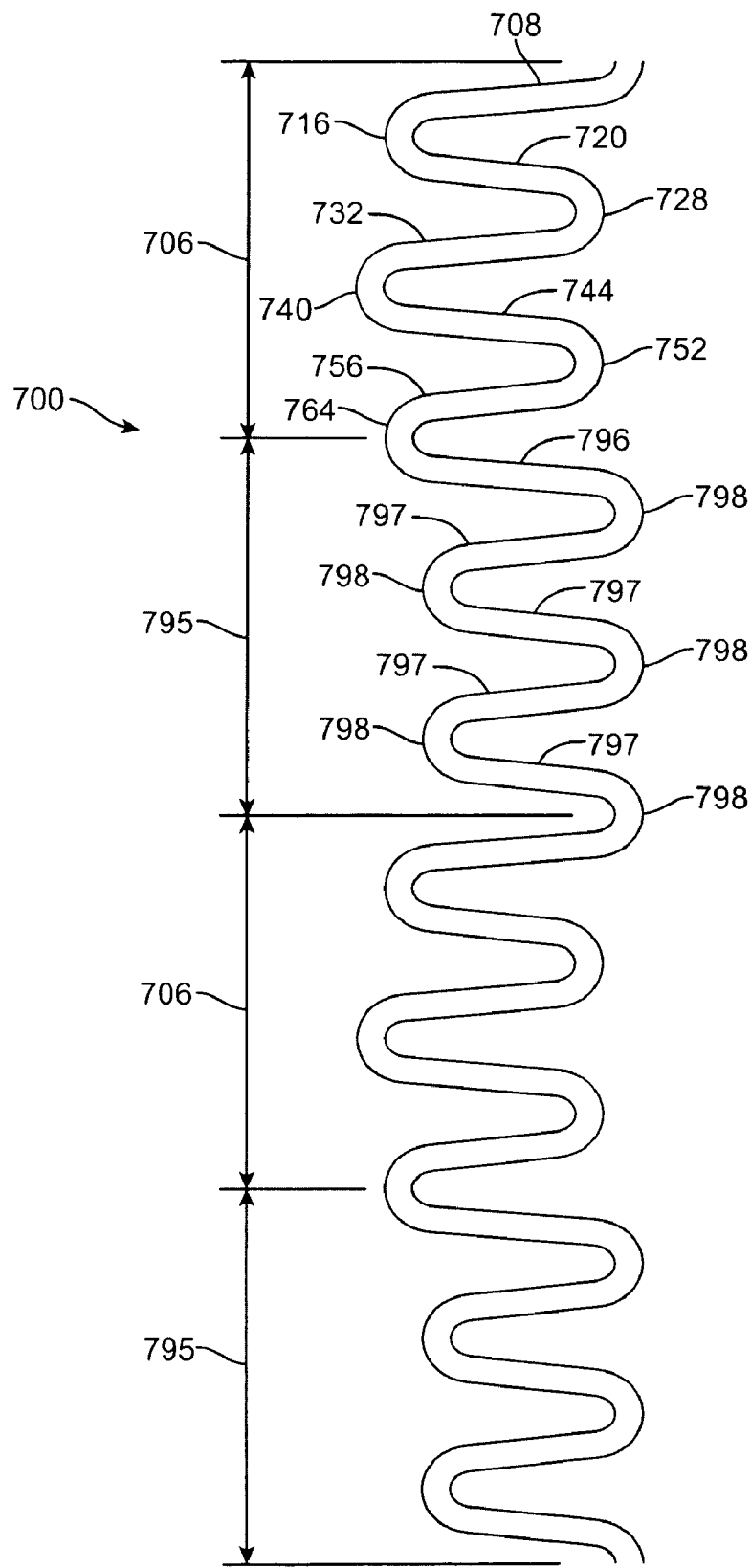
FIG. 7 is a plan view of a flattened band according to another embodiment of the present invention.

FIG. 7 shows another embodiment of the present invention, illustrated as a flattened band 700. Like band 100, band 700 is a wire having an undulating pattern. The pattern includes a repeating series 706 of segments and turns. Like series 106 of FIG. 1, the series 706 has five total segments, including a long segment 708, a first short segment 720, a first mid-sized segment 732, a second mid-sized segment 744, and a second short segment 756. First and second mid-sized segments 732, 744 are preferably the same length, while first and second short segments 720, 756 are preferably the same length. Short segments 720, 756 are shorter than mid-sized segments 732, 744 and mid-sized segments 732, 744 are shorter than long segment 708. The order of the five segments of series 706 has a LSMMS configuration (long, short, mid-sized, mid-sized, short).

In addition, the series 706 has five total turns, including a first turn 716, a second turn 728, a third turn 740, a fourth turn 752, and a fifth turn 764. These turns form valleys and peaks, in which peaks face the opposite longitudinal direction than valleys. The five turns 716, 728, 740, 752, and 764 connect the segments 708, 720, 732, 744, and 756 of the series 706 together in the same fashion described above with respect to series 106. Since third turn 740 is connected to first mid-sized segment 732 and second mid-sized segment 744, third turn 740 is longitudinally offset from peaks or valleys formed by first and fifth turns 716, 764.

Figure 8:
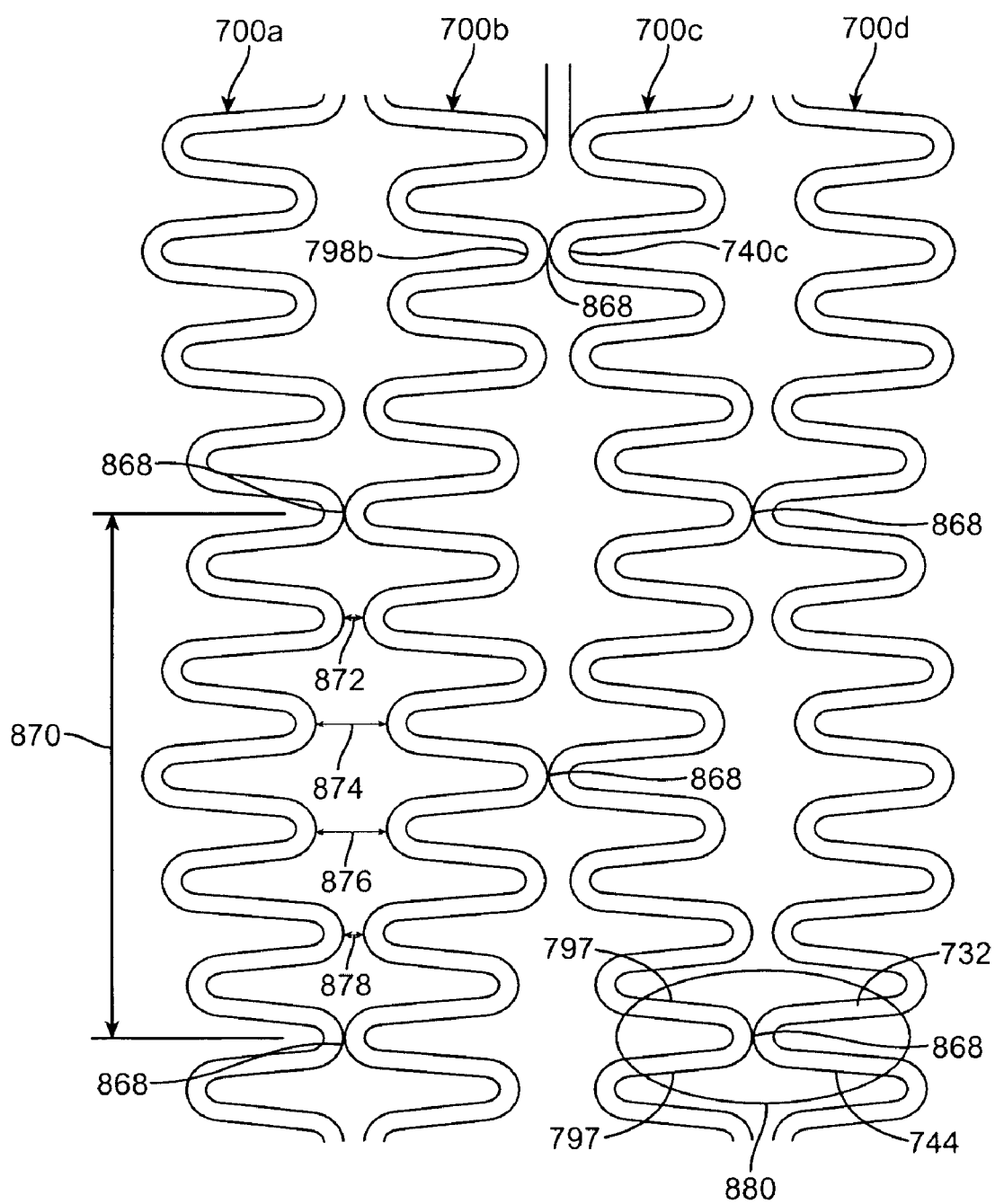
FIG. 8 is a plan view of four flattened aligned bands according to the embodiment illustrated in FIG. 7 with connections between adjacent bands.

Unlike the embodiment of FIGS. 1-4, in the embodiment depicted in FIGS. 7-8, series 706 is connected to a different adjacent series 795 (i.e., a series which does not have the LSMMS configuration of series 106 and series 706). Series 795 includes a total of five segments: a long segment 796 followed by four short segments 797. The five segments are connected together by five turns 798. Long segment 796 is preferably substantially the same length as long segment 708 of series 706, but may be different. Further, short segments 597 are preferably substantially the same length as short segments 720, 756 of series 706, but may be different. Band 700 of FIG. 7 illustrates a total of four series connected together in the following order: a first series 706, a first series 795, a second series 706, and a second series 795.

FIG. 8 shows a stent having four bands 700 (700a, 700b, 700c, and 700d) connected at connections 868. Bands 700a, 700b, 700c, and 700d are functionally the same. Band 700b is a mirror image of band 700a, and band 700d is a mirror image of band 700c. Therefore, bands 700a, 700b, 700c, and 700d each include a substantially similar pattern of segments and turns forming peaks and valleys. The bands are aligned to form adjacent bands such that the closed end of every other turn of a band is aligned with the closed end of every other turn of an adjacent band.

At least one connection 868 is formed between aligned closed ends of turns of adjacent bands. In this embodiment of FIG. 8, connections 868 occur at each of the offset peaks and valleys of a band formed by having first and second mid-sized segments 732, 744 on either side of the peak or valley. In other words, the offset peaks and valleys formed by third turns 740 of a band are connected to the peaks and valleys formed at one of turns 798 of an adjacent band. The offset peaks and valleys of each band 700a, 700b, 700c, and 700d are formed by the third turns 740 of the repeating series 706 as described above, having first and second mid-sized segments 732, 744 on either side of the third turn. For example, connection 868 is illustrated on FIG. 8 between third turn 740c of series 706 on band 700c and the third turn 798b of series 795 on adjacent band 700b.

Connections 868 are preferably formed by welding the turns together, such as by resistance welding, friction welding, laser welding or another form of welding such that no additional materials are used to connect bands 700. Alternatively, bands 700 can be connected by soldering, by the addition of a connecting element between the turns, or by another mechanical method. Further, as discussed above, the stent may be formed pre-connected as a unitary structure, such as by laser cutting or etching the entire stent body from a hollow tube or sheet. Other connections or ways to connect bands would be apparent to one skilled in the art and are included herein.

When adjacent bands 700 are connected together, a series 870 of consecutive tapered gaps is formed between consecutive unconnected aligned closed ends of turns of adjacent bands. The series 870 of consecutive tapered gaps allows the stent to flex with little or no interference between adjacent bands when the stent is tracked around a small radius bend in a vessel.

The series 870 of consecutive tapered gaps includes four gaps 872, 874, 876, 878 between connections 868. If first and second mid-sized segments 832, 844 are the same length and first and second short segments 820, 856 are the same length, gaps 874 and 876 will be of equal length and gaps 872 and 878 will be of equal length. Due to the length of long segment 808, gaps 874 and 876 are generally larger than gaps 872 and 878. The consecutive tapered nature of series 870 is advantageous in that larger gaps 874, 876 optimally occur between turns of adjacent bands which generally experience interference when the stent is tracked around a small radius bend in a vessel. Smaller gaps 872, 878 also add to the stent body's flexibility, while simultaneously providing greater scaffolding than that provided by larger gaps 874, 876. Greater scaffolding means that more area of the vessel walls is being supported directly by parts of the stent.

In addition to providing flexibility through the series of consecutive tapered gaps 870, the embodiment depicted in FIGS. 7-8 also incorporates a minimized rigid element 880. As explained above with respect to FIG. 3, minimizing the length of the longest rigid element of the stent further improves flexibility. The longest rigid element of a stent body occurs at the location of a connection 868. Connection 868 and the longest two segments on either side of connection 868 essentially form a rigid element which must be tracked around the bends of a vessel. By minimizing the length of this rigid element, the length which must be tracked around the bends of a vessel is shortened and thus the stent is easier to advance. As described above, connections 868 occur at the offset peaks and valleys of a band formed by mid-sized segments 732, 744 of a series 706. In other words, the peaks and valleys formed by first and second mid-sized segments 732, 744 of each band 700 are connected to an aligned closed end of a turn 798 of series 795 in an adjacent band. The length of rigid element 880 is decreased since mid-sized segments 732 and 744 occur on one side of connection 868. In this embodiment, the length of rigid element 880 is further decreased since short segments 797 of series 795 occur on the other side of connection 868.

Figure 10:
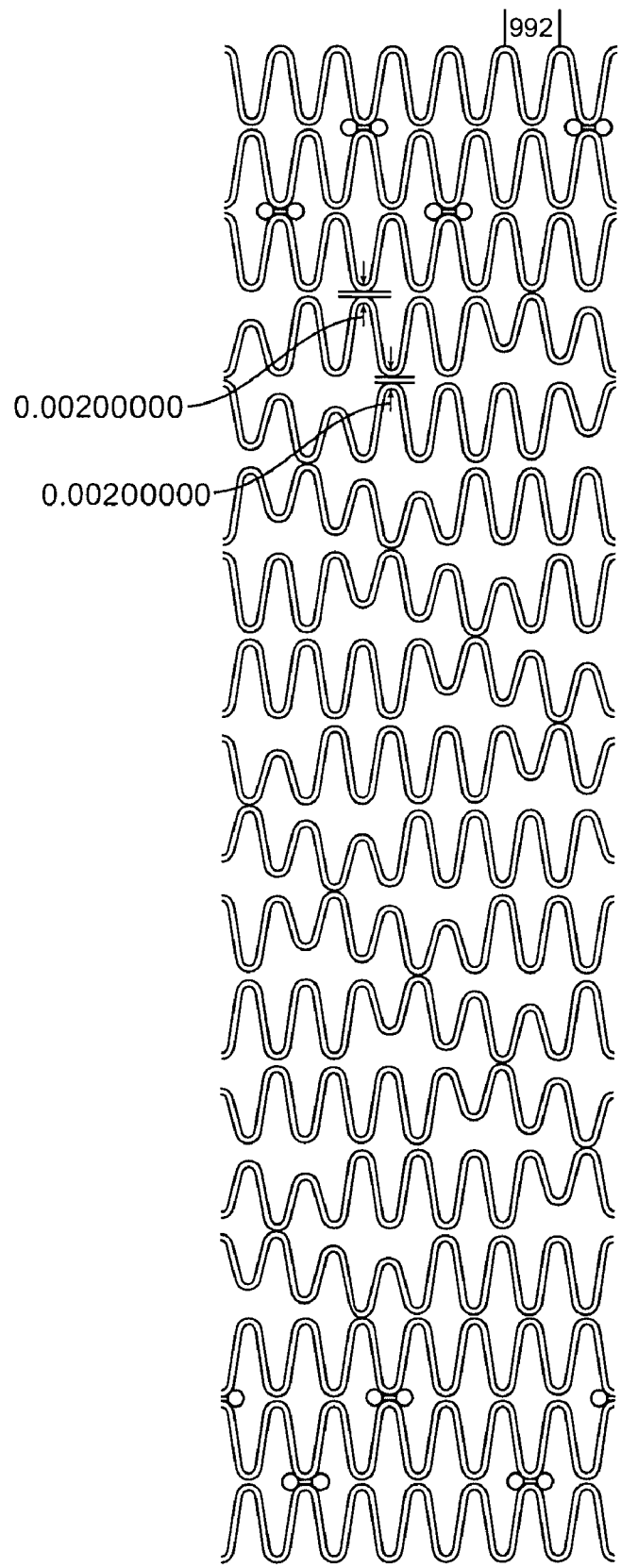
FIG. 10 is a plan view of a stent having multiple flattened aligned bands according to another embodiment of the present invention with connections between adjacent bands.

FIG. 10 shows an alternate embodiment of the present invention. FIG. 10 illustrates a stent having more than two bands connected together.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An intraluminal stent device, comprising: at least two bands including a first band and a second band, the first and second bands each including a substantially similar pattern of segments and turns forming peaks and valleys, the first band being aligned with the second band such that peaks of the first band are aligned with valleys of the second band; at least one connection formed between a peak of the first band and a valley of the second band; and a series of consecutive gaps formed between consecutive unconnected peaks of the first band and valleys of the second band, wherein the series of consecutive gaps includes four gaps in the following order: first smaller gap, first larger gap, second larger gap, second smaller gap, wherein the first and second larger gaps are larger than the first and second smaller gaps.

2. The intraluminal stent device of claim 1, wherein said pattern includes a first series of a long segment connecting with a first turn, said first turn connecting with a first short segment, said first short segment connecting with a second turn, said second turn connecting with a first mid-sized segment, said first mid-sized segment connecting with a third turn, said third turn connecting with a second mid-sized segment, said second mid-sized segment connecting with a fourth turn, said fourth turn connecting with a second short segment, and said second short segment connecting with a fifth turn.

3. The intraluminal stent device of claim 2, wherein said fifth turn connects with a second adjacent series, said second adjacent series being identical to said first series.

4. The intraluminal stent device of claim 2, wherein said fifth turn connects with a second adjacent series, said second adjacent series being different from said first series.

5. The intraluminal stent device of claim 4, wherein said second adjacent series includes five long segments connected by five turns.

6. The intraluminal stent device of claim 4, wherein said second adjacent series includes one long segment and four short segments connected by five turns.

7. The intraluminal stent device of claim 2, wherein said first short segment is the same length as said second short segment.

8. The intraluminal stent device of claim 2, wherein said first mid-sized segment is the same length as said second mid-sized segment.

9. The intraluminal stent device of claim 2, wherein said connections occur only at each third turn of each band, except for the first and last bands of the stent device.

10. The intraluminal stent device of claim 1, wherein said connections are formed by welding.

11. The intraluminal stent device of claim 1, wherein said adjacent bands are formed connected from a unitary structure.

12. The intraluminal stent device of claim 1, wherein at least two bands are placed onto a balloon of a balloon catheter for expansion within a body lumen.

13. The intraluminal stent device of claim 1, further comprising:
a third band including a pattern of segments and turns forming peaks and valleys, the third band being aligned with the second band such that valleys of the third band are aligned with peaks of the second band; and
at least two connections formed between a peak of the second band and a valley of the third band;
wherein the at least one connection between the first band and the second band comprises at least two connections;
wherein the at least two connections between the second band and the third band are circumferentially offset from the at least two connections between the first band and the second band.

14. The intraluminal stent device of claim 13, wherein at least one of the connections between the second band and the third band is disposed midway between at least one of the connections between the first band and the second band.

* * * * *